(12) United States Patent  
Gulliver et al.

(10) Patent No.: US 11,883,603 B2  
(45) Date of Patent: Jan. 30, 2024

(54) LOCKING TUBE CLIP

(71) Applicant: Fisher & Paykel Healthcare Limited, Auckland (NZ)

(72) Inventors: Laurence Gulliver, Auckland (NZ); Michael Paul Ronayne, Auckland (NZ); Puqing Zhang, Auckland (NZ); Andrew Paul Maxwell Salmon, Auckland (NZ); Rex Gordon Faithfull, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 17/645,368

(22) Filed: Dec. 21, 2021

(65) Prior Publication Data

US 2022/0218935 A1 Jul. 14, 2022

Related U.S. Application Data

(63) Continuation of application No. 16/875,148, filed on May 15, 2020, now Pat. No. 11,235,122, which is a
(Continued)

(51) Int. Cl.
*A61M 16/08* (2006.01)
*A61M 5/14* (2006.01)
(Continued)

(52) U.S. Cl.
CPC ........... *A61M 16/0875* (2013.01); *A61B 5/01* (2013.01); *A61M 5/1418* (2013.01); *F16L 3/12* (2013.01);
(Continued)

(58) Field of Classification Search
CPC ............ A61M 16/0875; A61M 5/1418; A61M 2039/087; A61M 2209/082;
(Continued)

(56) References Cited

U.S. PATENT DOCUMENTS 2,897,535 A 8/1959 Franklin
D204,159 S 3/1966 Piasecki
(Continued)

FOREIGN PATENT DOCUMENTS

GB 2142376 1/1985
WO WO 2010/131189 8/2010
WO WO 2012/122311 9/2012

OTHER PUBLICATIONS

International Search Report; PCT/NZ2012/000169; dated May 8, 2013; 5 pages.
(Continued)

*Primary Examiner* — David M Upchurch
(74) *Attorney, Agent, or Firm* — Knobbe, Martens, Olson & Bear, LLP

(57) ABSTRACT

A component useable with one or more tube comprises a body engageable with one or more external surface recesses of the one or more tubes. The component has a pair of jaws extending from the body for gripping an item. The component is configured, such that, in use, in a first orientation of the body relative to the respective tube(s) recesses, the component is movable along a length of the tube(s); and, in a second orientation of the body relative to the respective tube(s) recesses, the component is resistive to movement along a length of the tube(s).

18 Claims, 12 Drawing Sheets

Related U.S. Application Data continuation of application No. 16/228,306, filed on Dec. 20, 2018, now Pat. No. 10,688,268, which is a continuation of application No. 15/886,772, filed on Feb. 1, 2018, now Pat. No. 10,195,387, which is a continuation of application No. 14/346,287, filed as application No. PCT/NZ2012/000169 on Sep. 21, 2012, now Pat. No. 9,919,125.

(60) Provisional application No. 61/537,759, filed on Sep. 22, 2011.

(51) Int. Cl.
| *F16L 3/12* | (2006.01) |
|---|---|
| *F16L 3/13* | (2006.01) |
| *F16L 3/237* | (2006.01) |
| *A61B 5/01* | (2006.01) |
| *F16L 3/23* | (2006.01) |
| *A61M 39/08* | (2006.01) |

(52) U.S. Cl.
CPC ............... *F16L 3/13* (2013.01); *F16L 3/237* (2013.01); *A61M 2039/087* (2013.01); *A61M 2209/082* (2013.01); *A61M 2209/088* (2013.01)

(58) Field of Classification Search
CPC ....... A61M 2209/088; A61B 5/01; F16L 3/12; F16L 3/13; F16L 3/237
See application file for complete search history.

(56) References Cited

U.S. PATENT DOCUMENTS

| | | | |
|---|---|---|---|
| 3,473,768 A | 10/1969 | Piasecki | |
| 3,535,746 A | 10/1970 | Thomas, Jr. | |
| 4,371,137 A | 2/1983 | Anscher | |
| 4,564,163 A * | 1/1986 | Barnett | H02G 3/32 24/297 |
| 4,707,906 A | 11/1987 | Posey | |
| 4,765,335 A | 8/1988 | Schmidt | |
| 4,795,197 A * | 1/1989 | Kaminski | F16L 25/0045 285/903 |
| 5,015,013 A * | 5/1991 | Nadin | H02G 3/0691 285/903 |
| 5,079,802 A | 1/1992 | Blase et al. | |
| 5,159,731 A | 11/1992 | Dereadt | |
| 5,188,609 A | 2/1993 | Bayless et al. | |
| 5,316,247 A | 5/1994 | Wodka | |
| 5,400,776 A | 3/1995 | Bartholomew | |
| 5,423,501 A * | 6/1995 | Yu | F16L 3/233 248/62 |
| 5,653,411 A * | 8/1997 | Picco | H02G 3/263 24/339 |
| 6,301,756 B1 | 10/2001 | Howard | |
| 6,513,767 B1 | 2/2003 | Rodgers | |
| 6,568,716 B1 | 5/2003 | Fieber | |
| 6,595,473 B2 | 7/2003 | Aoki et al. | |
| 6,636,679 B1 * | 10/2003 | Mereness | G02B 6/4471 385/136 |
| 6,854,694 B1 | 2/2005 | Van Etten | |
| D521,367 S | 5/2006 | Blanton | |
| 7,240,930 B2 * | 7/2007 | Stravitz | D06F 58/20 285/903 |
| 7,581,292 B2 | 9/2009 | Votel | |
| 7,963,487 B2 | 6/2011 | Saltenberger et al. | |
| 8,025,643 B2 * | 9/2011 | Bierman | A61M 25/02 604/174 |
| 8,231,147 B2 * | 7/2012 | Link | F16L 33/035 285/420 |
| 9,919,125 B2 | 3/2018 | Gulliver et al. | |
| 9,956,930 B2 | 5/2018 | Loebe | |
| 10,195,387 B2 | 2/2019 | Gulliver et al. | |
| 10,688,268 B2 | 6/2020 | Gulliver et al. | |
| 11,235,122 B2 | 2/2022 | Gulliver et al. | |
| 2003/0005554 A1 | 1/2003 | Nagayasu | |
| 2007/0282272 A1 | 12/2007 | Bannon | |
| 2008/0051731 A1 | 2/2008 | Schweikert et al. | |
| 2008/0078397 A1 | 4/2008 | Scott et al. | |
| 2008/0092349 A1 | 4/2008 | Cofer | |
| 2010/0148015 A1 * | 6/2010 | Matsuno | F16L 3/1075 248/65 |
| 2010/0164226 A1 * | 7/2010 | Serizawa | F16L 3/1091 285/149.1 |
| 2010/0280459 A1 | 11/2010 | Werner | |
| 2010/0294271 A1 * | 11/2010 | Pittaway | A61M 5/1418 128/202.13 |
| 2010/0299892 A1 * | 12/2010 | Ardern | F16B 2/08 24/481 |
| 2014/0120494 A1 | 5/2014 | Chin | |
| 2014/0151514 A1 | 6/2014 | Asai | |
| 2014/0236041 A1 | 8/2014 | Gulliver | |
| 2016/0343496 A1 | 11/2016 | Mukuno et al. | |

OTHER PUBLICATIONS

Written Opinion; PCT/NZ2012/000169, dated May 8, 2013; 8 pages.
Qosina, Bedding clip Qosina product, Medical accessories clip; https://web.archive.org/web/20160312061730/https:/www.qosina.com/sheet-clip-black-34003, as early as Mar. 12, 2016.
Fisher & Paykel Healthcare, Respiratory Humidification Products, as early as Jun. 2004, 41 pages.
Fisher & Paykel Healthcare, Respiratory Humidification| Single Use & Reusable Product Catalogue early as 2008, 70 pages.

\* cited by examiner

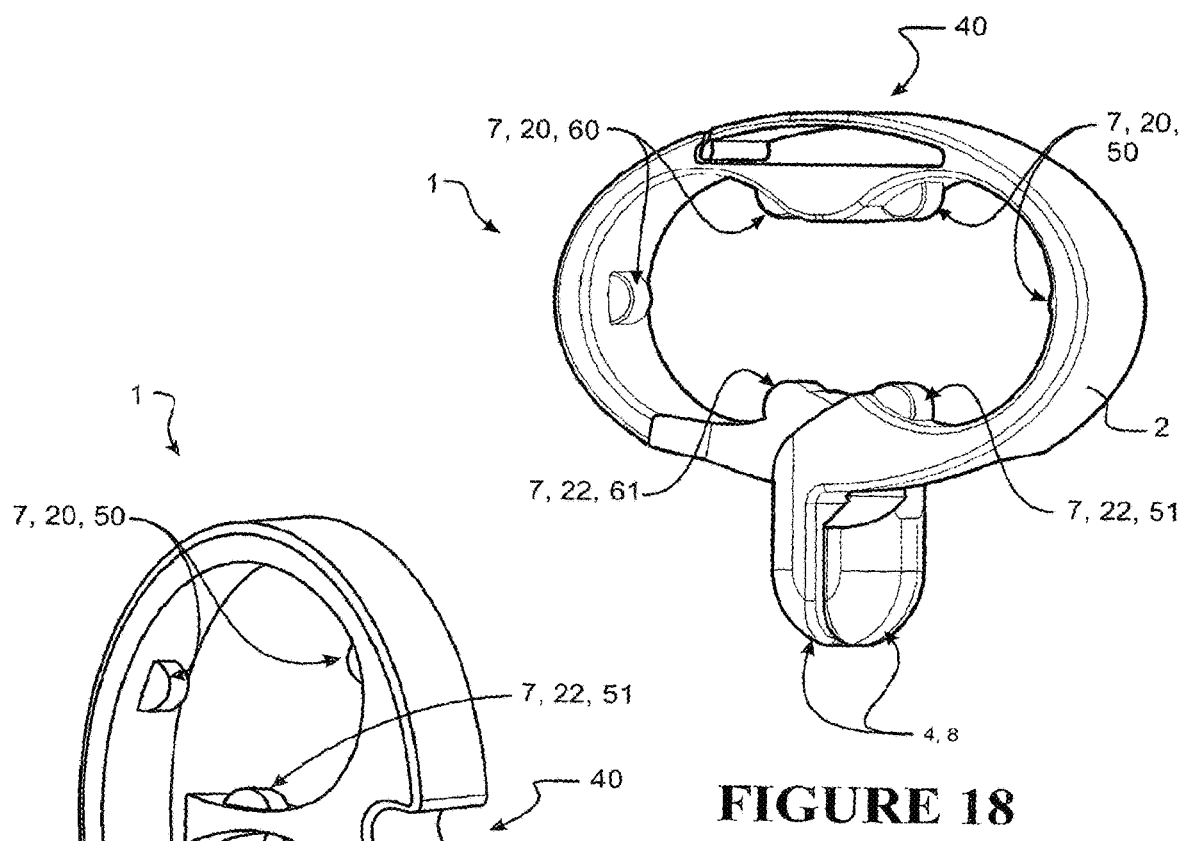
FIGURE 18
FIGURE 19
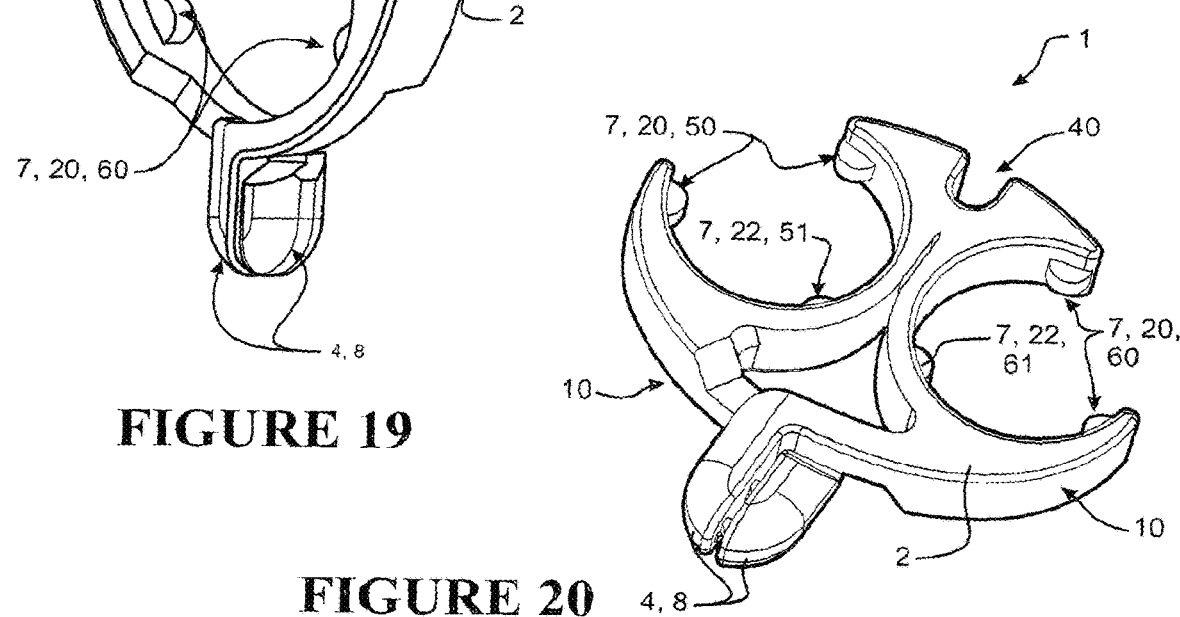
FIGURE 20

LOCKING TUBE CLIP

INCORPORATION BY REFERENCE TO ANY PRIORITY APPLICATIONS

The present application is a continuation application of U.S. patent application Ser. No. 16/875,148, filed on May 15, 2020, which is a continuation application of U.S. patent application Ser. No. 16/228,306, filed Dec. 20, 2018, now U.S. Pat. No. 10,688,268, issued Jun. 23, 2020, which is a continuation application of U.S. patent application Ser. No. 15/886,772, filed Feb. 1, 2018, now U.S. Pat. No. 10,195,387, issued Feb. 5, 2019, which is a continuation application of U.S. patent application Ser. No. 14/346,287, filed Mar. 20, 2014, now U.S. Pat. No. 9,919,125, issued Mar. 20, 2018, which is a 371 of International PCT/NZ2012/000169, filed Sep. 21, 2012, which claims priority benefit of U.S. Provisional Application Ser. No. 61/537,759, filed on Sep. 22, 2011, the disclosures of each of which are hereby incorporated by reference in their entireties.

FIELD OF THE INVENTION

The present invention relates to components for medical circuits. In one particular aspect, the invention relates to a component locatable about the exterior surface of a corrugated breathing tube, such as for use in the inspiratory and/or expiratory limb of a breathing circuit, or for corrugated tubes associated with surgical insufflation systems.

BACKGROUND TO THE INVENTION

In medical applications, such as with assisted breathing, the gases inhaled by a patient or user are preferably delivered in a condition having humidity near saturation level and at close to body temperature (usually at a temperature between 33° C. and 37° C.). In facilitating delivery of gases to a patient in such preferred conditions, breathing tubes (or medical tubes) may be used. Such tubes may take various shapes and configurations. One generally used configuration is (at least) an externally corrugated tube.

In various instances, the corrugated tubing is advantageously placed or positioned in certain locations relative to the patient or user. For example, the tubing may need to be held in a position or supported such that the weight of the tubing such not exert forces on the patient or user or other associated medical devices they may be using, such as masks or other interfaces. Enabling the positioning, support and adjustment of tubing between various further positioned or supported positions for patients or users would be beneficial.

In this specification, where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Further aspects and advantages of the present invention will become apparent from the ensuing description which is given by way of example only.

SUMMARY OF THE INVENTION

It is an object of the present invention to provide a component for use with a medical circuit that will at least go some way towards improving on the above or which will at least provide the public or the medical profession with a useful choice.

In a first aspect, the present invention may be said to broadly consist in a component for use with one or more tubes, the component comprising a body engageable with one or more external surface recesses of respective one or more tubes, and a pair of jaws extending from the body for gripping an item such that, in use, in a first orientation of the body relative to the respective tube(s) recesses, the component is movable along a length of the tube(s), and in a second orientation of the body relative to the respective tube(s) recesses, the component is resistive to movement along a length of the tube(s).

Preferably in use, the body is substantially surrounding of a perimeter of the tube(s).

Preferably an internal surface of the body is engageable with the one or more external surface recesses of the tube(s).

Preferably in the first orientation the component is in a plane such that the body engageable with external recesses of the respective tube(s) is substantially co-axial with the respective tube(s), and in the second orientation the component is in a plane such that the body is engageable with external recesses of the respective tube(s) is substantially non co-axial with the respective tube(s).

Preferably one or more portions extend from the body to be engageable with the recesses of the tube(s).

Preferably the one or more portions is/are fixed portions.

Preferably the one or more portions is/are an annular lip or a projection or projections extending from an internal surface of the body.

Preferably the jaws are opposing upon one another in a closed position.

Preferably the jaws are co-acting upon each other in a closed position.

Preferably the jaws are hingedly biased toward each other in reaching a substantially closed position.

Preferably the jaws are openable from a substantially closed position for gripping of an item, openable by deflecting the jaws away from each other.

Preferably the jaws are openable and grippable of an item for locating of the tube engaged by the component in a set position.

Preferably the component is positioned on the tube(s), such that, when the component is in the second orientation, and the jaws are gripping of an item, the component acts to locate the tube(s) in a set position.

Preferably the item comprises one or more of the following: clothing, bedding, structures associated with personal clothing (e.g. personal lanyard, belt) or bedding (e.g. bed frame, mattress), structures associated with medical equipment or where a user is located (e.g. stands, bed side table), incubators, or cots.

Preferably the body comprises a shoulder portion associated with each jaw of the pair of jaws, the shoulder portion providing a surface for actuation, by a user, of the jaws to an open position.

Preferably the shoulder portion is an enlarged region of the body.

Preferably in use, the shoulder portions are deflectable towards each other, such that, in-use, deflection moves the jaws from a closed or substantially closed position to or toward a substantially open position, and release of the deflection allows the hingedly biased jaws to move back to the closed or substantially closed position.

Preferably the shoulder portions are sized for actuation by fingers of a user, or are finger tabs.

Preferably one or each jaw comprises grips for gripping of an item.

Preferably the grips are one or a series of ridges, projections or teeth, such grips being interlockable or interposing with one or more corresponding grips of an opposing jaw.

Preferably one of more of the grips is shaped to expose one or a series of acute angled portions facing inwardly toward the body.

Preferably one of more of the grips is shaped to expose one or a series of obtusely angled portions facing outwardly away from the body.

Preferably the body is configured to be substantially annular about the exterior surface of the, or each, respective tube(s).

Preferably the body further comprises at least one retainer portion for retaining of an accessory.

Preferably the accessory is an electrical cable, or sensor cable (such as a temperature probe cable), or a lanyard.

Preferably the accessory is a temperature probe cable.

Preferably the retainer portion is a recessed region of the body.

Preferably the body configured to be engageable with two or more tubes.

Preferably the body is configured to substantially surround two or more tubes.

Preferably the body engageable with one or more external surface recesses of the respective one or more tubes comprises, for each respective tube: at least one first projection engageable with a corresponding first recess of a respective tube, and at least one second projection engageable with the same first or another recess, of the same respective tube.

Preferably in the first orientation, the internal surface of the body comprises, for each of the respective one or more tubes: at least one first projection engageable with a corresponding first recess of a respective tube, and at least one second projection engageable with the same or another recess, of the same respective tube, located near the first recess in which the at least one first projection is engageable.

Preferably in the second orientation, the internal surface of the body comprises, for each of the respective one or more tubes: the at least one first and at least one second projections engaged with a recess or recesses of each respective tube, wherein the engaged recesses of each respective tube are separated from one another by a distance along the length of each of the respective tube(s).

Preferably in the second orientation, the at least one first and at least one second projections act on each of the respective tube(s), or its recesses or a part thereof, to restrain the component from being moved between recesses or along a length of the respective tube(s).

Preferably there are two first projections, and a single second projection.

Preferably in the first orientation, the two first projections are engageable with a corresponding first recess of a first of one or more respective tube(s), and the single second projection is engageable with the same or another recess of the same first respective tube located near the first recess in which the at least one first projection is engageable.

Preferably in the second orientation, the two first projections are engageable with a corresponding first recess of the first of the one or more respective tube(s), and the single second projection is engageable with a recess of the same first respective tube separated from the first recesses by a distance along the length of the same first respective tube.

Preferably the body is engageable with one or more external surface recesses of a pair of tubes, the body comprising: at least one first projection engageable with a corresponding first recess of a first respective tube, and at least one second projection engageable with the same first or another recess, of the same first respective tube, and at least one further first projection engageable with a corresponding first recess of a second respective tube, and at least one further second projection engageable with the same first or another recess, of the same second respective tube.

Preferably body comprises at least one lip for engaging with at least one recess of the or each respective tube(s).

Preferably the lip is one or a series of projections extending substantially annularly about a surface of the body and being respectively engageable with the one or more external surface recesses of the or each respective tube(s).

Preferably the tube(s) is a medical breathing tube.

Preferably the tube is a medical breathing tube. For example, a medical breathing tube is defined by International standard ISO 5367:2000(E) (Fourth edition, 2000-06-01).

The term "comprising" as used in this specification is open and means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Preferred embodiments of the invention will be described by way of example only and with reference to the drawings, in which:

FIGS. 15, 16, 17, 18 and 19 show a component configured for engaging with a pair of tubes.

FIG. 20 shows a further embodiment of a component configured for engaging with a pair of tubes.

DETAILED DESCRIPTION OF THE INVENTION

In this specification, the terms "medical circuit" and "breathing circuit" are used to indicate the general field of the invention. It is to be understood that a "circuit" is intended to include open circuits, which do not form a complete closed circuit. For example, CPAP systems typically consist of a single inspiratory breathing tube between the blower and the patient interface. The term "breathing circuit" is intended to include such "open circuits". Similarly, the term "medical circuit" is intended to include both breathing circuits and insufflation circuits, which are also typically "open." Similarly, the term "medical tubing" is intended to be read as flexible tubing suitable for use in the type of medical circuits described above connecting between components of a medical circuit and providing a low resistance gases pathway between components of a medical circuit.

Figure 14:
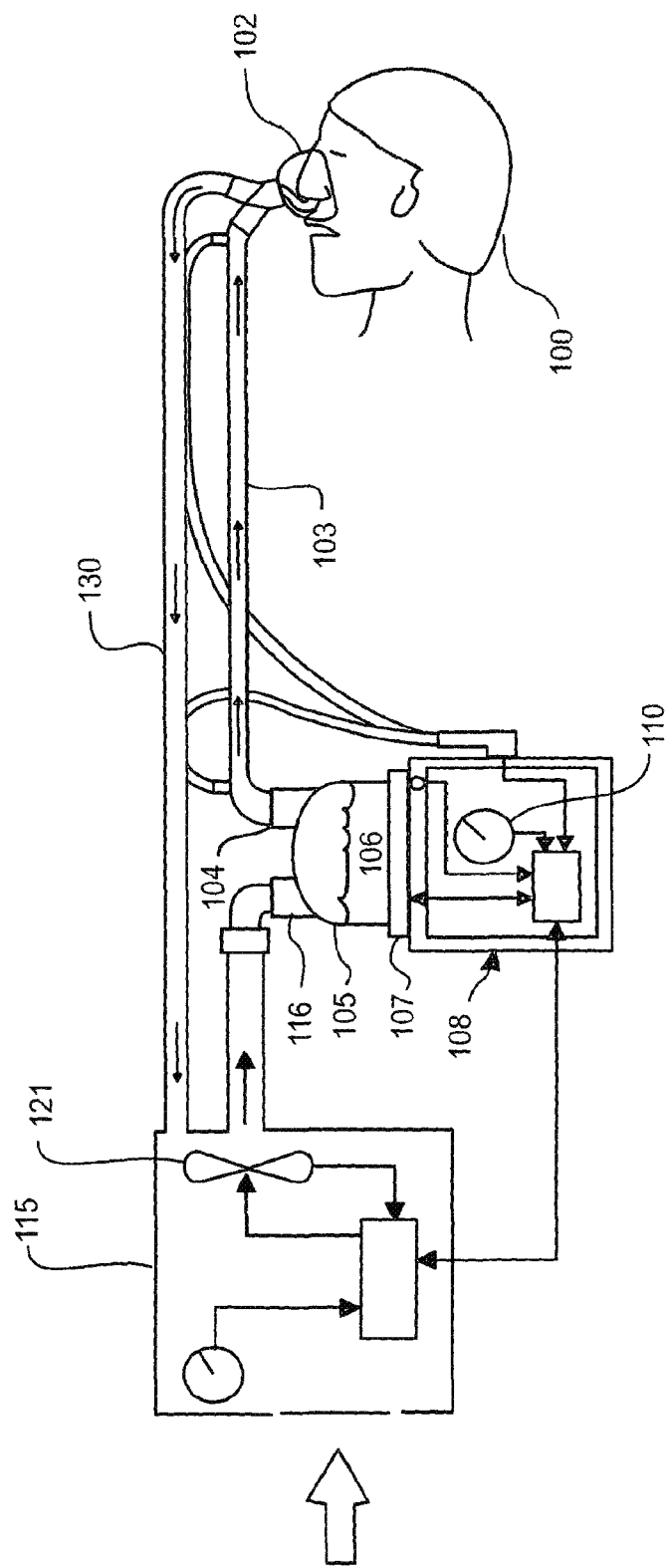
FIG. 14 generally illustrates one form of a medical circuit provided for a user, in providing a source of humidified breathing gas.
Figure 16:
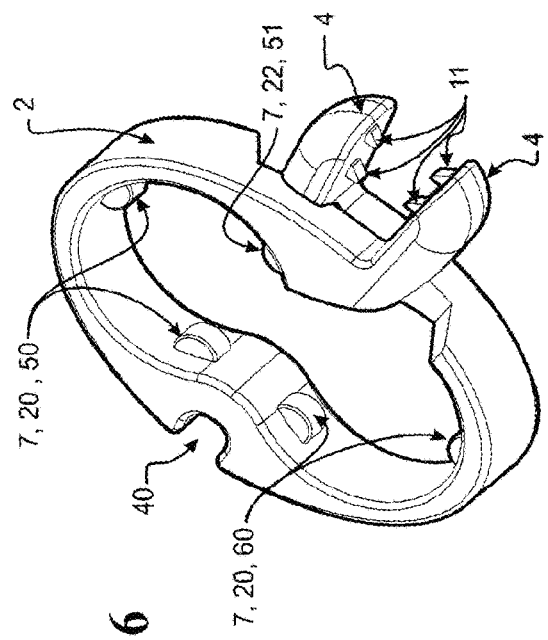
Figure 17:
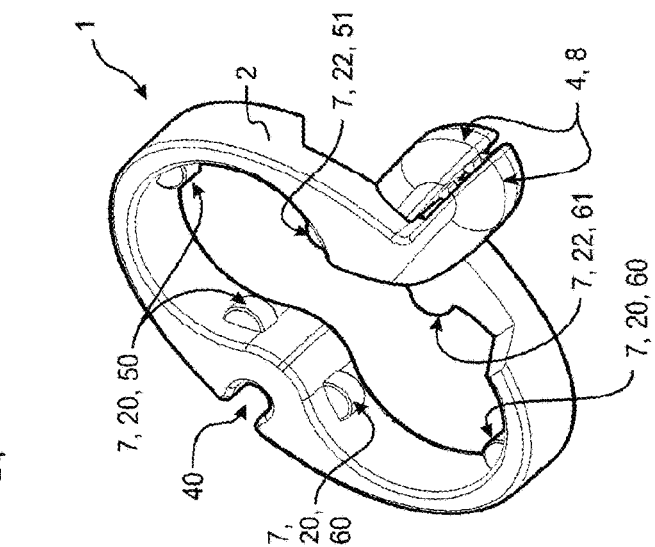
Figure 15:
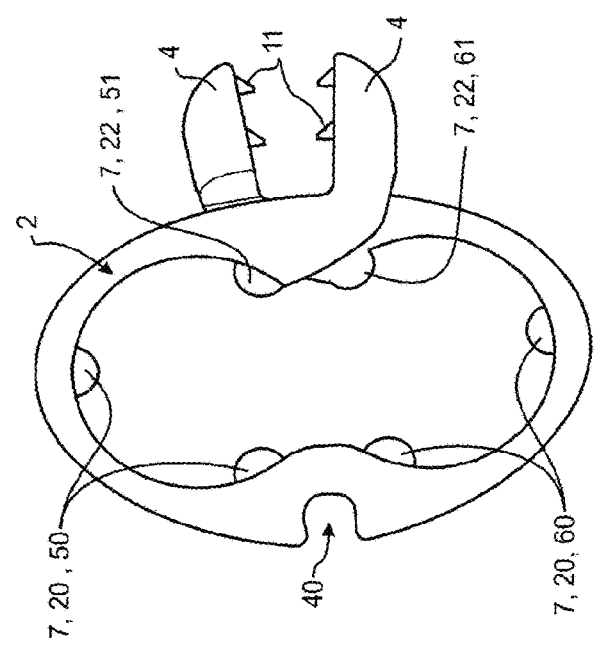

In the field of medical circuits, and in particular breathing circuits, including anaesthetic circuits, condensation or rain-out can be a particular problem where high humidity breathing gases come into contact with the walls of a component at a relatively lower temperature. With reference to FIG. 14, a humidified ventilation system is shown in which a patient 100 is receiving humidified and pressurised gases through a patient interface 102 connected to a humidified gases transportation pathway or inspiratory breathing tube 103. It will be appreciated the patient interface 102 may take the form of a nasal mask, oral mask, oronasal mask, nasal prongs, endotracheal tube or full-face mask, for example but without limitation.

It should be understood that delivery systems could also be continuous, variable or bi-level positive airway pressure or numerous other forms of respiratory therapy. The inspiratory tube 103 is connected to the outlet 104 of a humidification chamber 105 which contains a volume of water 106. The inspiratory tube 103 may include a heater or heater wires (not shown) which heat the humidified gases within the tube to reduce the formation of condensation. The humidification chamber 105 is heated by a heater plate 107 of humidifier base 108. The humidifier 108 is provided with an electronic controller which may comprise a microprocessor based controller executing computer software commands stored in associated memory.

In response to the user set humidity or temperature value input via dial 110, for example, and/or other inputs, the controller determines when (or to what level) to energise heater plate 107 to heat the water 106 within the humidification chamber 105. As the volume of water is heated, water vapour begins to fill the chamber above the water's surface and is passed out of the humidification chamber outlet 104. A flow of gases (for example, air) is provided from a gases supply or ventilator 115, which enters the chamber 105 through inlet 116. Exhaled gases from the patient's mouth are returned to the ventilator via a return expiratory breathing tube 130 that may also include a heater or heater wires (not shown), which heat the humidified gases within the expiratory breathing tube to reduce the formation of condensation.

It is preferable that medical tubing (for example the inspiratory and/or expiratory breathing tubes 103,130) is: resistant to crushing, resistant to restrictions in flow when bent (e.g., increased resistance to flow<50% when bent around a 1 inch cylinder), resistant to kinking, resistant to changes in length/volume under fluctuating internal pressure (e.g., resistance to compliance), resistant to leaking (e.g., <25 ml/min @6 kPa), have low flow resistance (e.g., increase in pressure@max. rated flow<0.2 kPa), electrically safe (e.g., resistant to sparks in the tubing) given an operating environment that may be oxygen-rich.

International standard ISO 5367:2000(E) (Fourth edition, 2000-06-01) is one example of how some of these desirable parameters are measured and quantified, and the document is hereby incorporated into this specification in its entirety by reference. It is preferable that components described herein meet or exceed some or all of these standards. Further, reference to medical tubes includes breathing tubes as defined in the above ISO standard.

In accordance with certain features, aspects and advantages of this invention, a component 1 is provided as an accessory for use with medical tubing. The components has particular application for the positioning and support of such medical tubing relative to a user or equipment associated with the user (e.g., user interfaces or patient interfaces, such as masks, nasal cannula and the like, briefly described above).

The ability to locate a medical tube relative to a user has certain advantages. Being able to help support the weight of the medical tubing connected to equipment associated with the user has a number of advantages including but not limited to, for example, reducing the weight transferred to a user or equipment associated with the user, which may in turn impact on the efficiency of a treatment being provided to a user, or the overall comfort experienced by a user when using such equipment.

Further, as a user moves or re-positions their body relative to the medical tubing or associated equipment, strain may be transferred to the tubing or to the user via the associated equipment. A relatively quick and effective re-positioning or re-locating of the tubing to provide support again would be useful. Certain features, aspects and advantages of the present invention attempt to provide or go at least some way towards providing at least an alternative component facilitating such advantages.

Such a component can be utilised to position or locate inspiratory or expiratory medical tubing, or other tubing associated with such medical circuits as described above. Particular application may have uses in the OSA fields, as well as in hospital situations.

According to the one aspect of the present invention, a component 1 is provided for use with a tube. The component 1 comprises a body 2 engageable with one or more external surface recesses 3 (or surface relief portions or sections) of a tube (e.g., such as those of a corrugated tube or tube with a helically recessed surface region). The component 1 includes a pair of jaws 4 that extend from the body 2. The jaws 4 can be used for attaching to or for gripping of an item (not shown). In use, in a first orientation 5 of the body 2 relative to the tube recesses 3, the component 1 is movable along a length of the tube. While in a second orientation 6 of the body 2 relative to the tube recesses 3, the component 1 is resistive to movement along a length of the tube.

In a further aspect, the component 1 provides for use with one or more tubes (not shown). The component 1 comprises a body 2 engageable with one or more external surface recesses 3 (or surface relief portions or sections) of respective one or more tubes. The one or more tubes (not shown) are receivable by the body 2, with the body 2 being engageable with the external recesses of such tubes. The component 1 includes a pair of jaws 4 extending from the body 2 for gripping an item (not shown). In use, in a first orientation 5 of the body 2 relative to the respective tube(s) recesses (e.g. corrugations of a tube or tubes), the component 1 is movable along a length of the tube(s), and in a second orientation 6 of the body relative to the respective tube(s) recesses, the component 1 is resistive to movement along a length of the tube(s).

Figure 2:
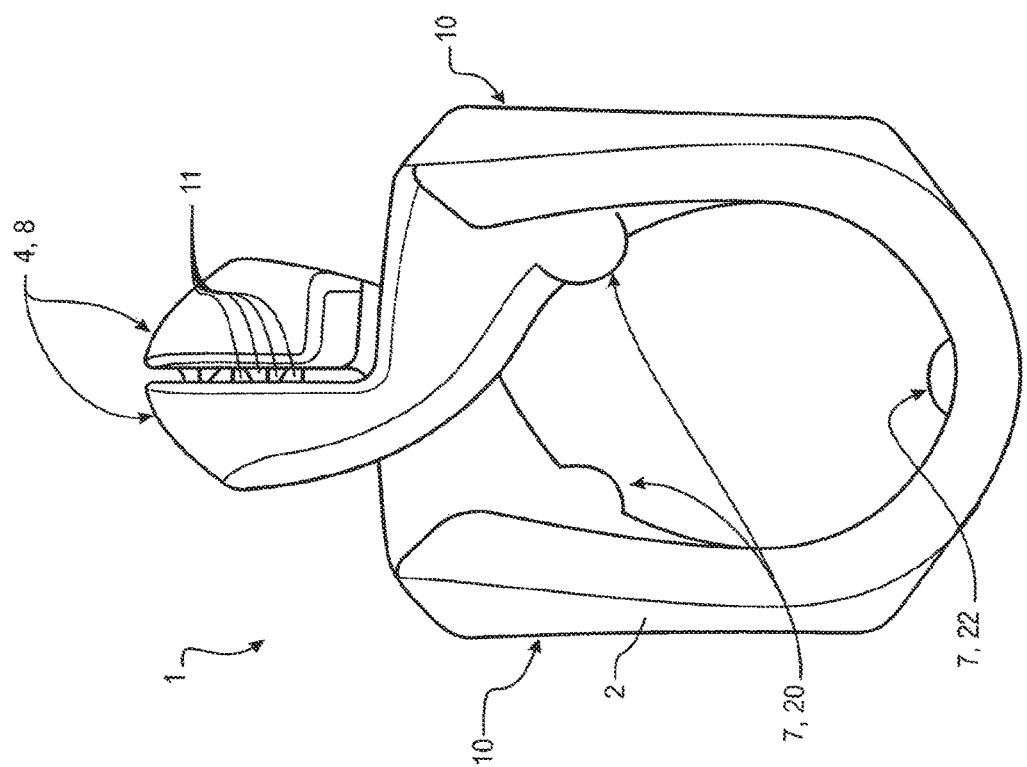
FIG. 2 is a side view of the embodiment shown in FIG. 1.
Figure 1:
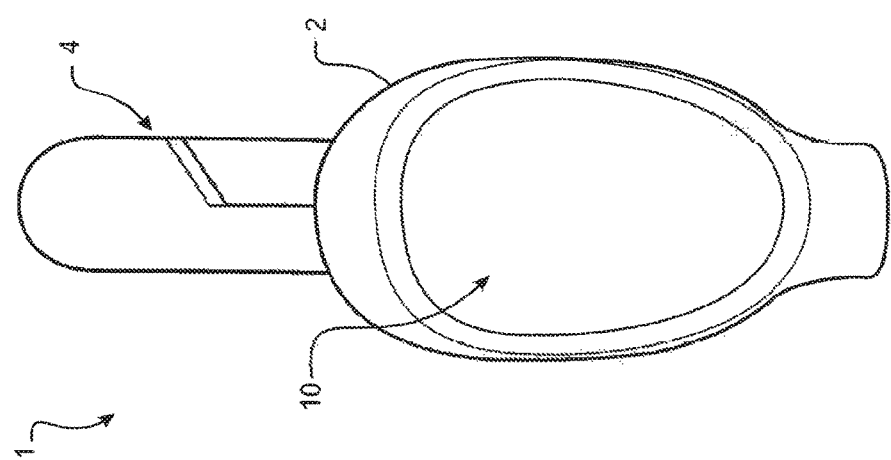
FIG. 1 is an end view of one embodiment of a component that is arranged and configured in accordance with certain features, aspects and advantages of the invention.

In respect of the above, it will be seen that FIGS. 1-2 show various embodiments of a component 1 and in relation to certain tubes of helical or axial corrugation. The general configuration and arrangement as shown for the first and second orientations of the embodiments of component 1 shown by FIGS. 15-20 will be accordingly understood with reference to those FIGS. 1-13B.

Advantageously, in the first orientation 5, the component 1 is oriented in a plane such that the body 2 is engageable with certain external recesses 3 of the tube when substantially co-axial with the tube. And, in the second orientation 6, the component 1 is oriented in a plane such that the body 2 is engageable with certain other external recesses 3 of the tube when substantially non co-axial with the tube. It will be appreciated, where for example the body 2 is configured for receiving two or more respective tubes, the component 1 is adapted to operate in the same manner.

Surface recesses 3 can include surface relief features, such as repeating recesses 3 or other surface relief features such as those of a corrugated tube, or a tube having a helical outer rib extending along the length of the tube being held or engaged therewith by body 2.

Figure 6A:
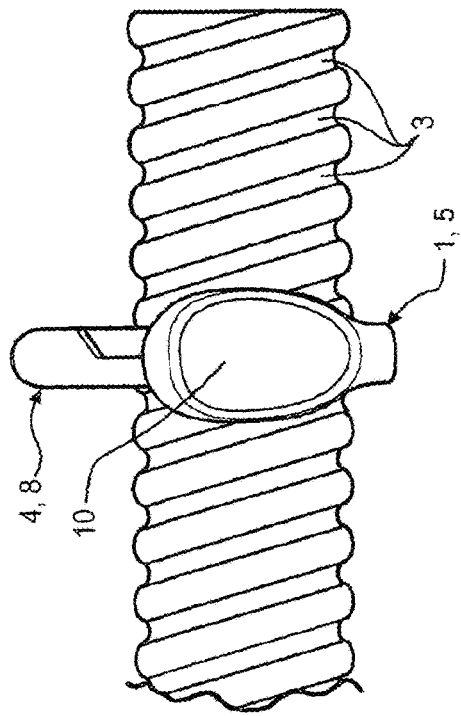
FIGS. 6A and 7A show a component in a first orientation relative to the tube about which it is positioned.
Figure 7A:
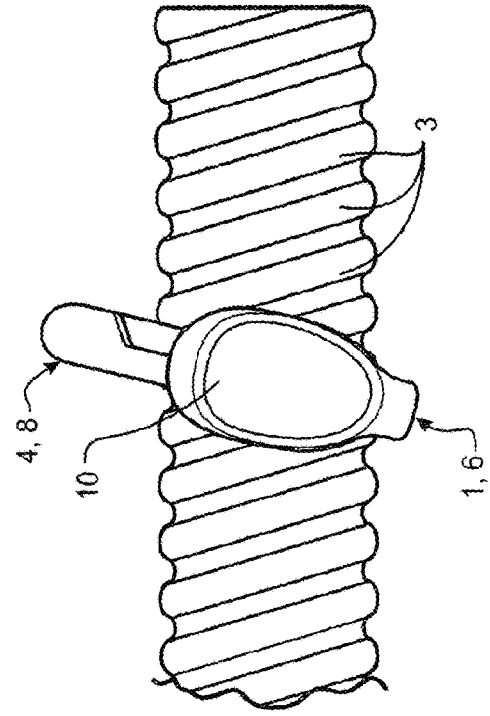
Figure 6B:
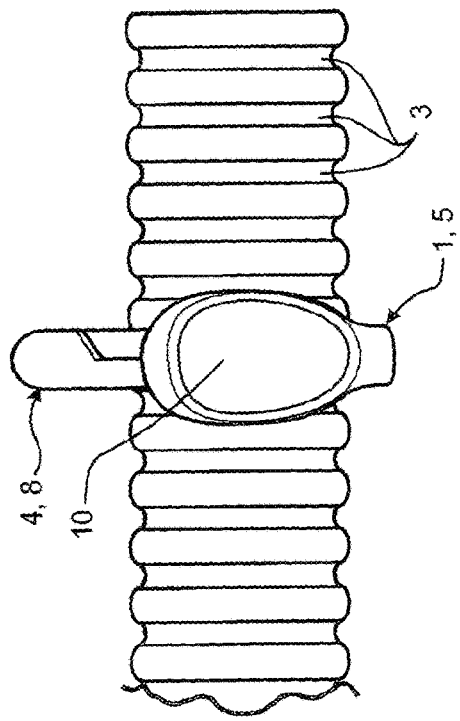
FIGS. 6B and 7B show a component in a second orientation relative to the tube about which it is positioned.
Figure 7B:
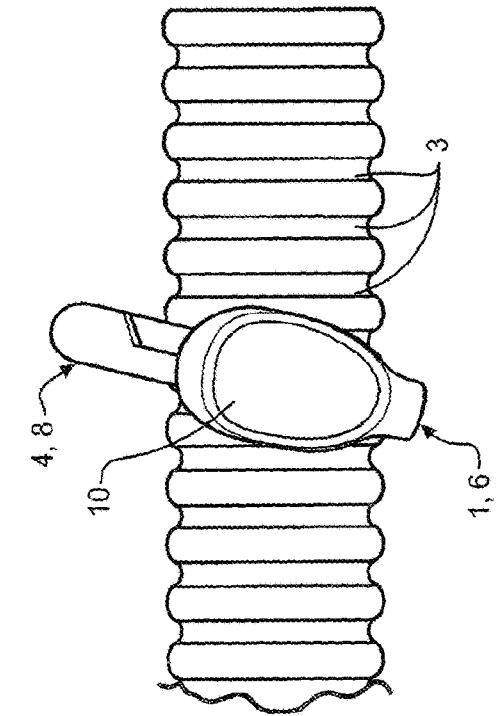
Figure 9:
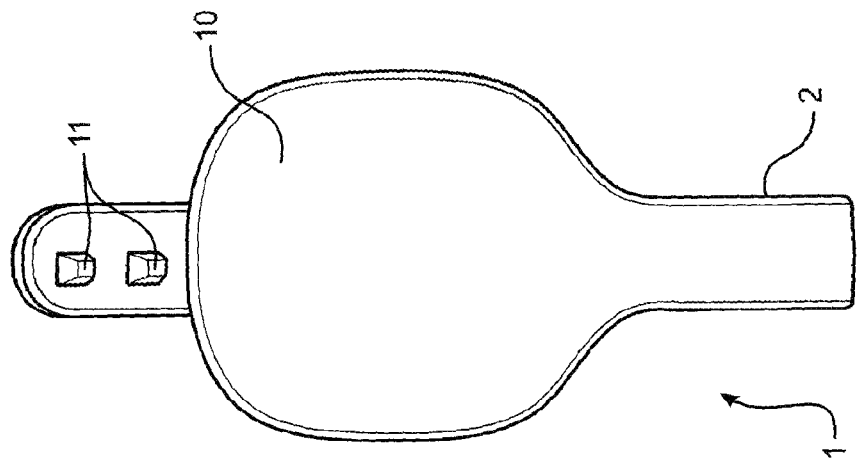
FIG. 9 is an end view of the component as shown in FIG. 8.
Figure 13B:
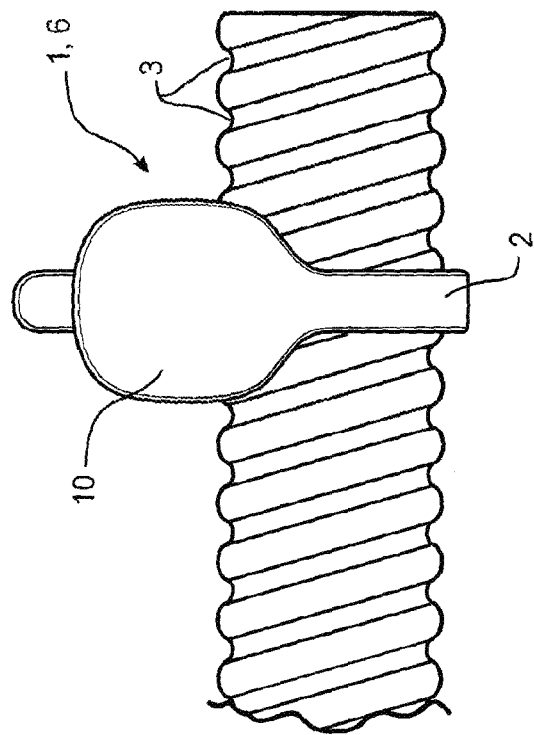
FIGS. 13A and 13B illustrate a first orientation of the component shown by FIGS. 8-12 about a tube.
Figure 13A:
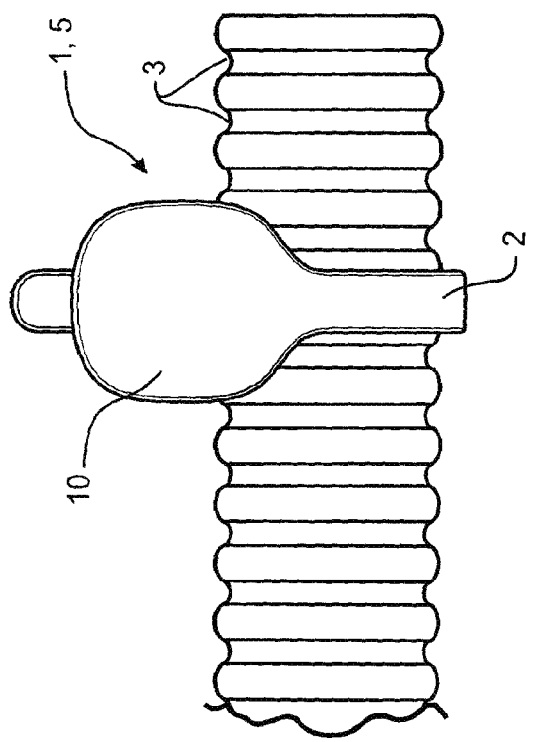

FIGS. 6A, 7A and 13A show two different embodiments of the component 1 in a first orientation 5 relative to a corrugated tube. FIGS. 6A, 6B and 13A show a component 1 in a position about a linearly corrugated tube, while FIGS. 7A, 7B and 13B show a component 1 in a position about a helically corrugated tube. It will be appreciated the component 1 will also operate in the same manner on a linearly or helically corrugated tube, or those tubes where the surface recesses 3 or relief features are ribs with interposed recesses 3, whether helical or linear relief features or ribs. The component 1 embodiments as shown by FIGS. 15-19 operate in the same manner, but are configured with a body 2 adapted to engage with a pair of tubes.

The body 2 substantially surrounds the perimeter, or circumference, of the tube(s), such that a portion or portions (such as projection 7 or 20, 22 or 30) of the body 2 are engageable with the surface recesses 3 or with surface relief portions or sections. Accordingly, the component 1 is enabled to be moved along the tube when in a first body orientation, yet the component 1 being resistive to being moved along the tube when in a second body orientation relative to the tube's recesses 3 or surface relief features.

Figure 5:
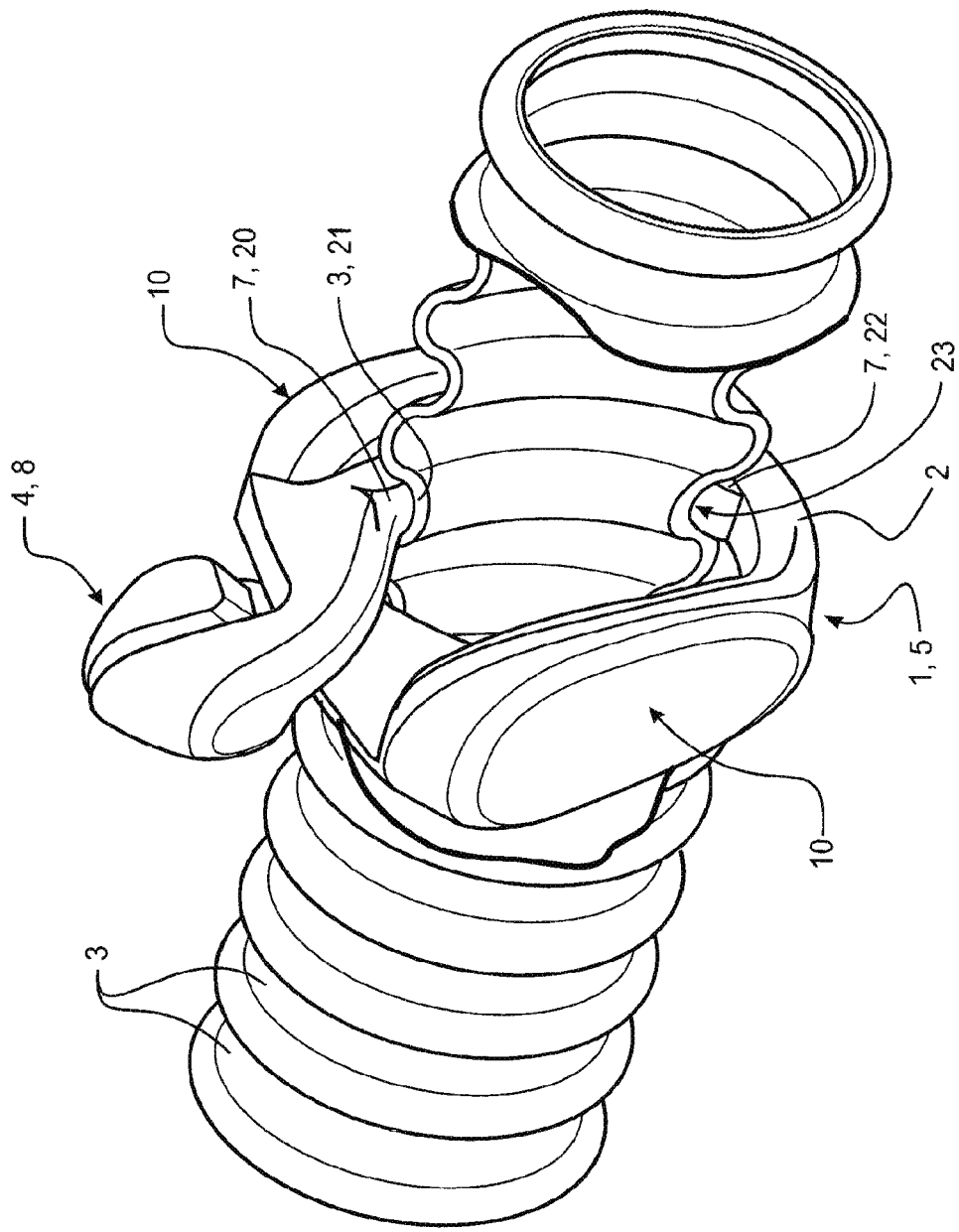
FIG. 5 shows the component of FIGS. 1-4 in-situ about a corrugated tube.
Figure 11:
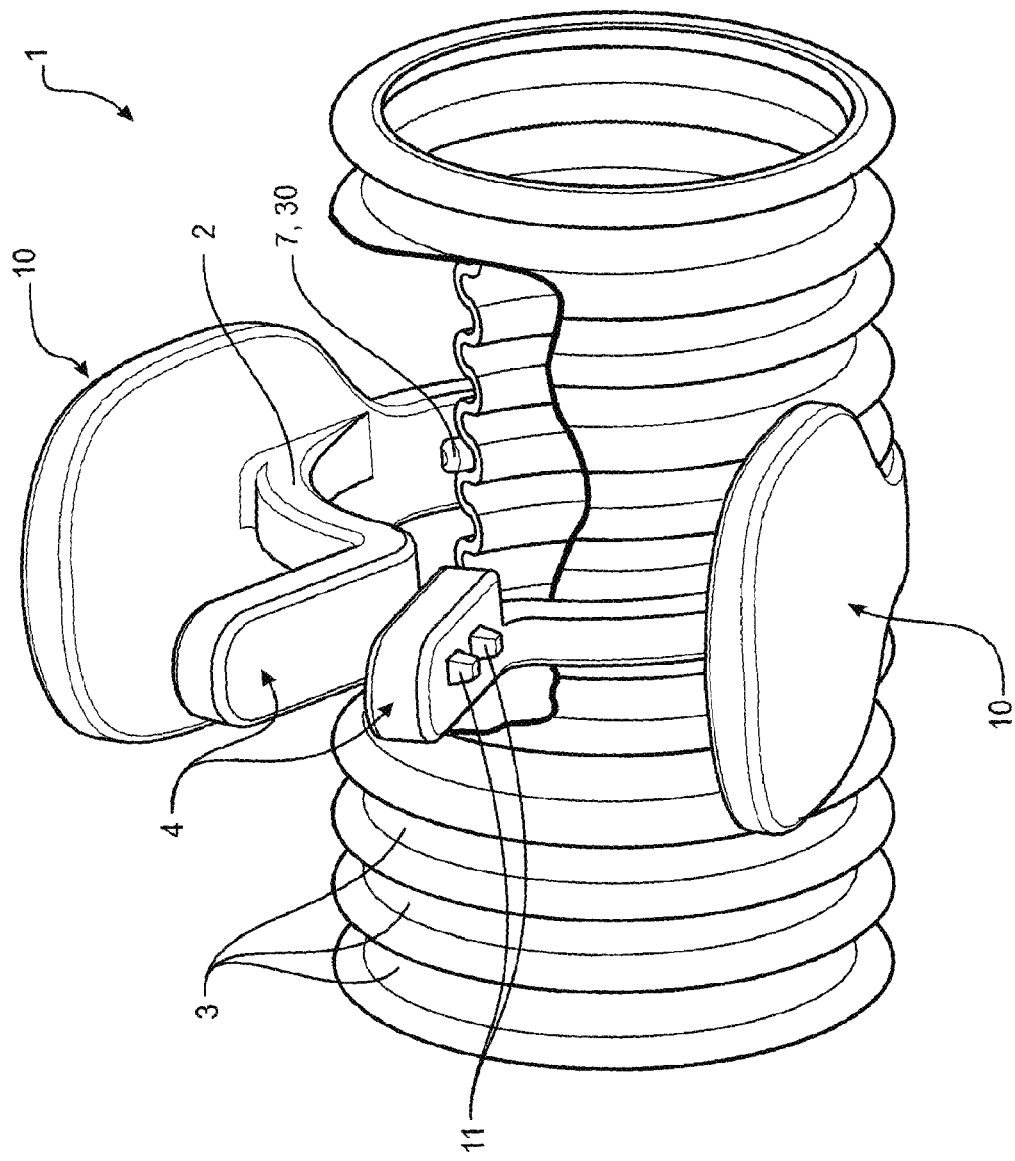
FIG. 11 shows the component of FIGS. 8-10 in an in-situ position about a tube, with jaws not yet moved into an operational arrangement.
Figure 12:
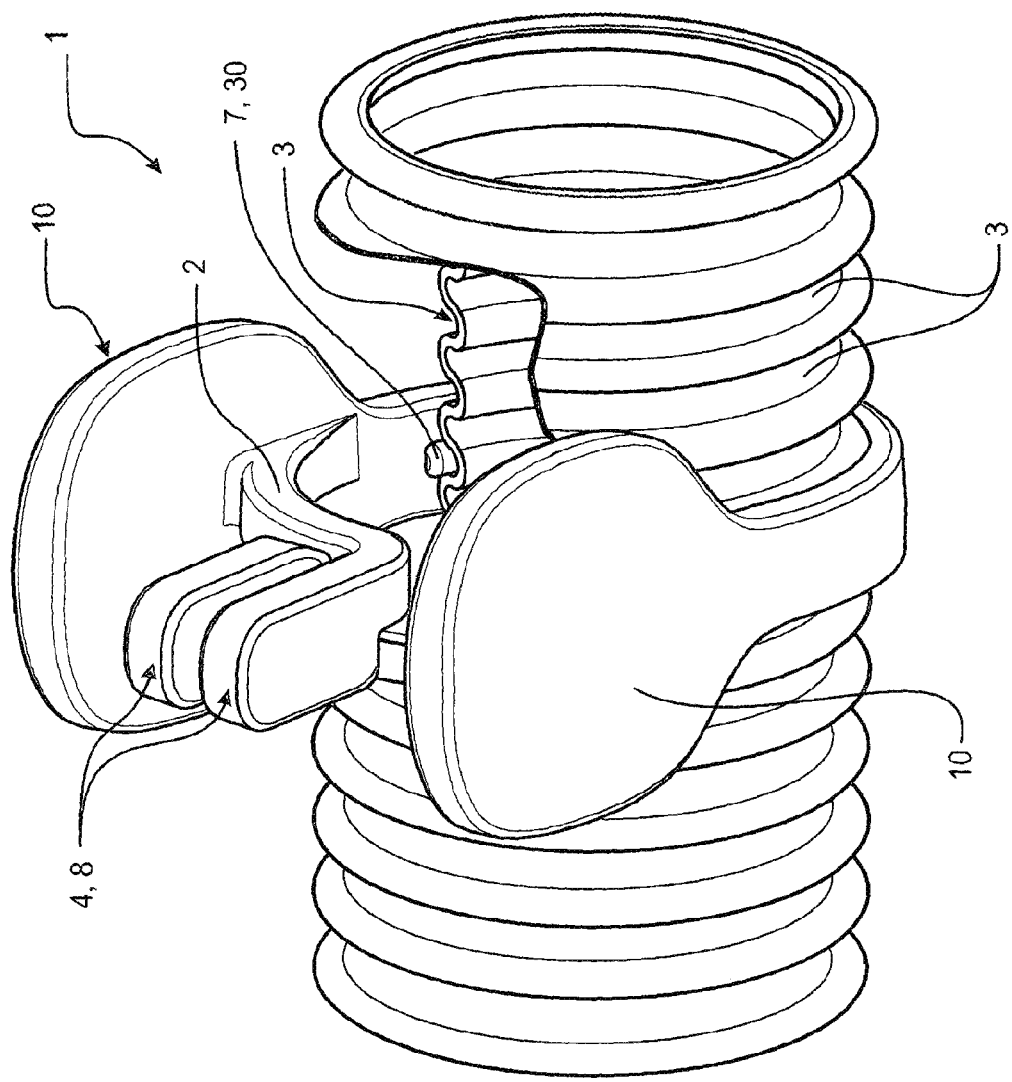
FIG. 12 shows the component of FIGS. 8-11 in an in-situ position about a tube, with jaws moved into their operational arrangement.

As a part of substantially surrounding the tube, an internal surface (or surfaces or portions of the internal surface) of the body 2 is or are engageable with the one or more external surface recesses 3 (or relief features) of the tube. In this manner, the body 2 may be substantially annular about the exterior surface of the tube being engaged. FIGS. 5, 11, 12 show such a component 1 in-situ about a tube, and illustrate how portions of the body 2 are engageable with surface recesses 3 or surface relief features of the tube to which the component 1 surrounds.

Turning to the jaws 4 of the component 1, in one preferred embodiment the jaws 4 are configured to be opposing upon one another, or co-acting on each other, when in their closed position 8. Such jaws 4, or other variations of these, may be configured such that they are hingedly biased toward each other in reaching a substantially closed position 8. Further, the jaws 4 can be openable from a substantially closed position 8 to enable the jaws 4 to receive and then close upon an item for gripping of that item. The jaws 4 can be openable by deflecting the jaws 4 away from each other. Manually actuating the jaws 4 to create such a deflection or opening is additionally facilitated by providing finger grips or tabs for the user of the component 1.

Figure 3:
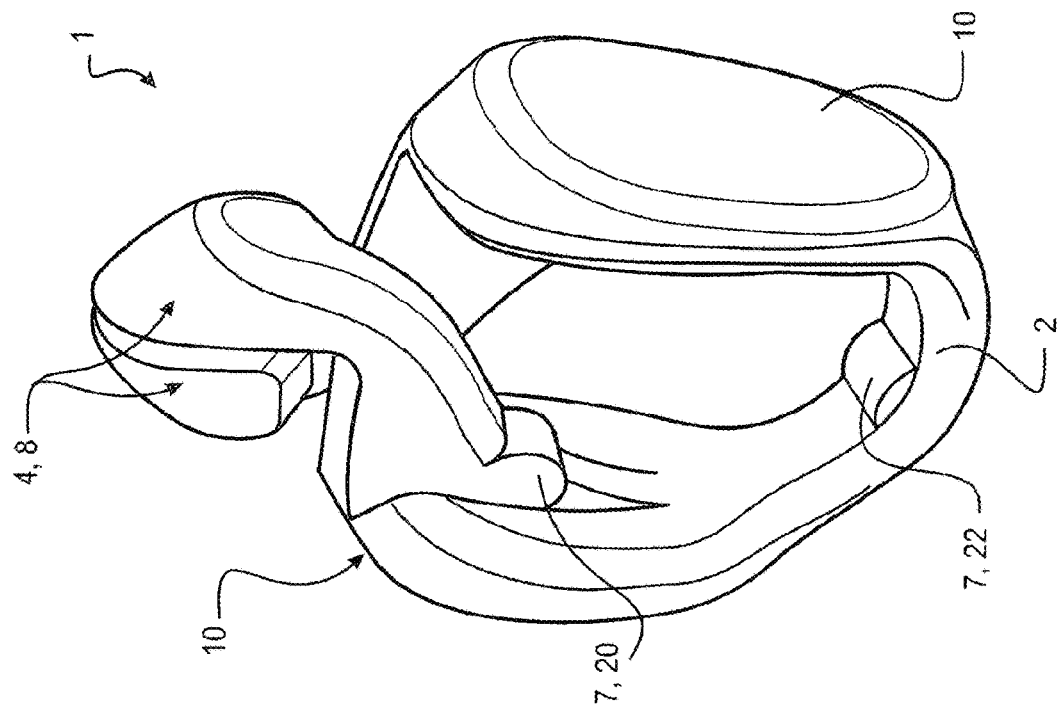
FIG. 3 is a top perspective view of a component according to certain features, aspects and advantages of the invention, with jaws yet to be moved into an opposing operational arrangement.
Figure 4:
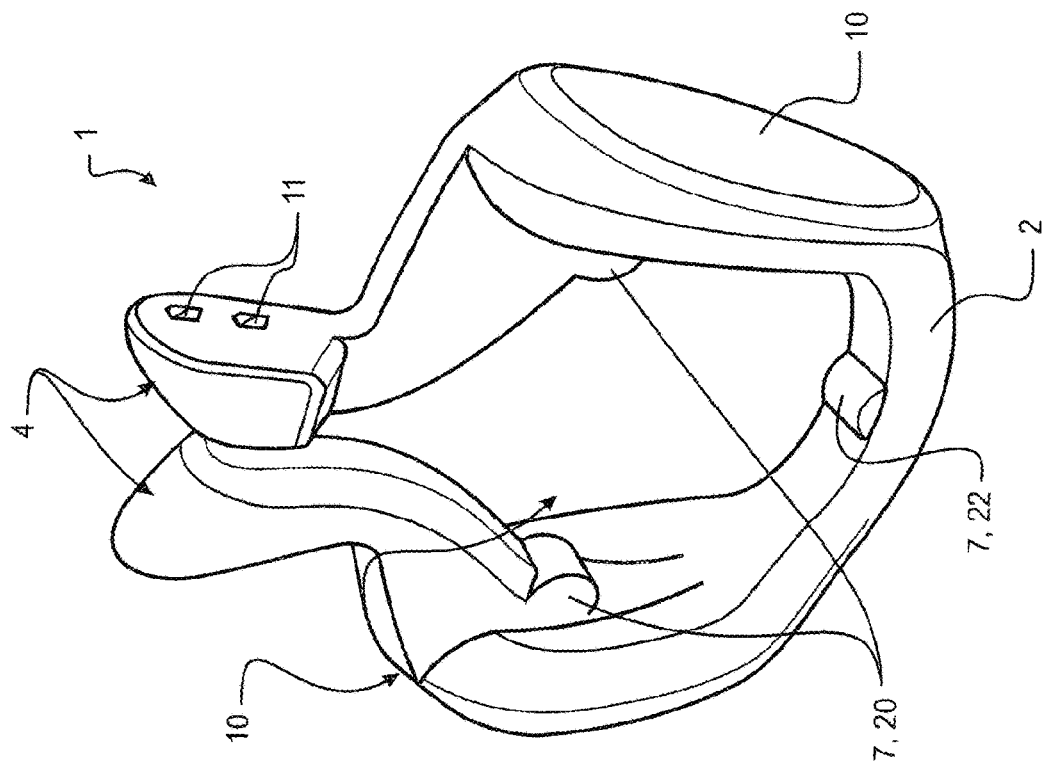
FIG. 4 is a further top perspective view of the component of FIG. 3, showing the jaws moved into their opposing operational arrangement.

FIG. 3 shows one embodiment of a component 1 where the jaws 4 are displaced and yet to be moved into a co-acting or opposing relationship with each other, FIG. 4 shows more clearly how the jaws 4 are arranged when the component 1 is provided for use, reference is also made to FIG. 2 showing the grips and inter-posing arrangement of the grips on the jaws 4.

Figure 8:
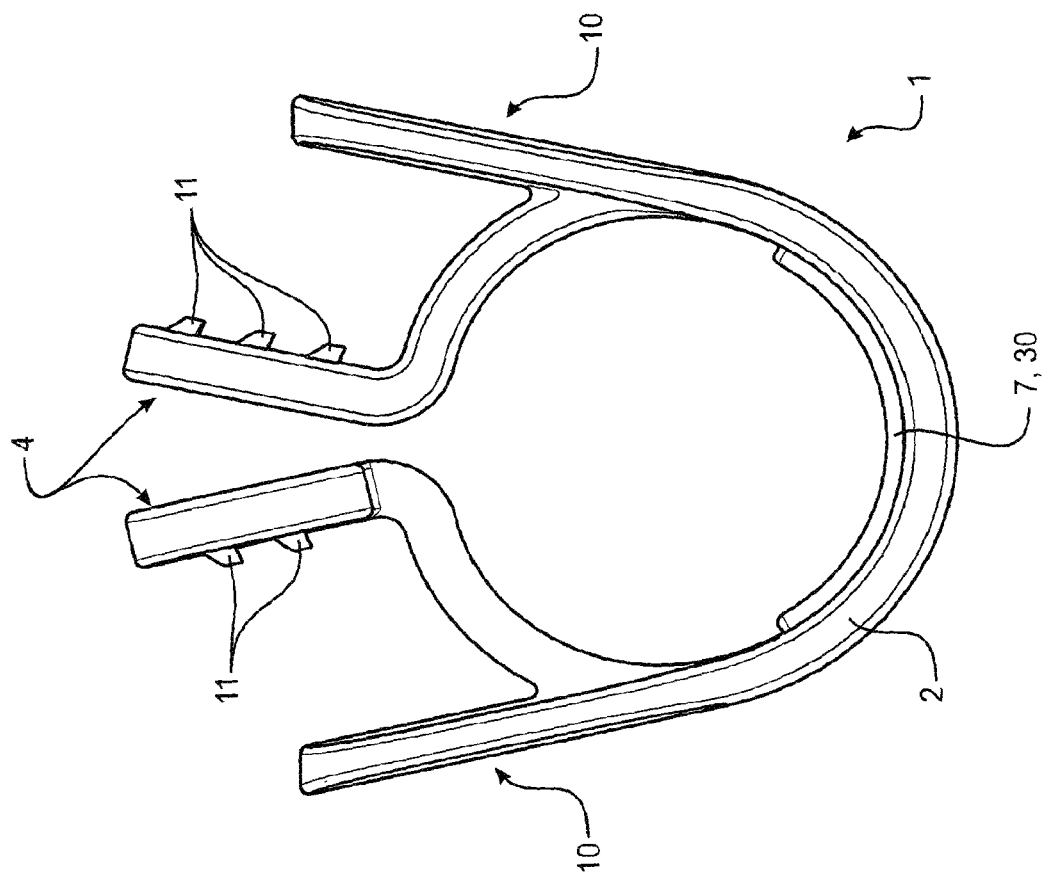
FIG. 8 is a side view of a further embodiment according to certain features, aspects and advantages of the invention, with jaws yet to be moved into their operational arrangement.
Figure 10:
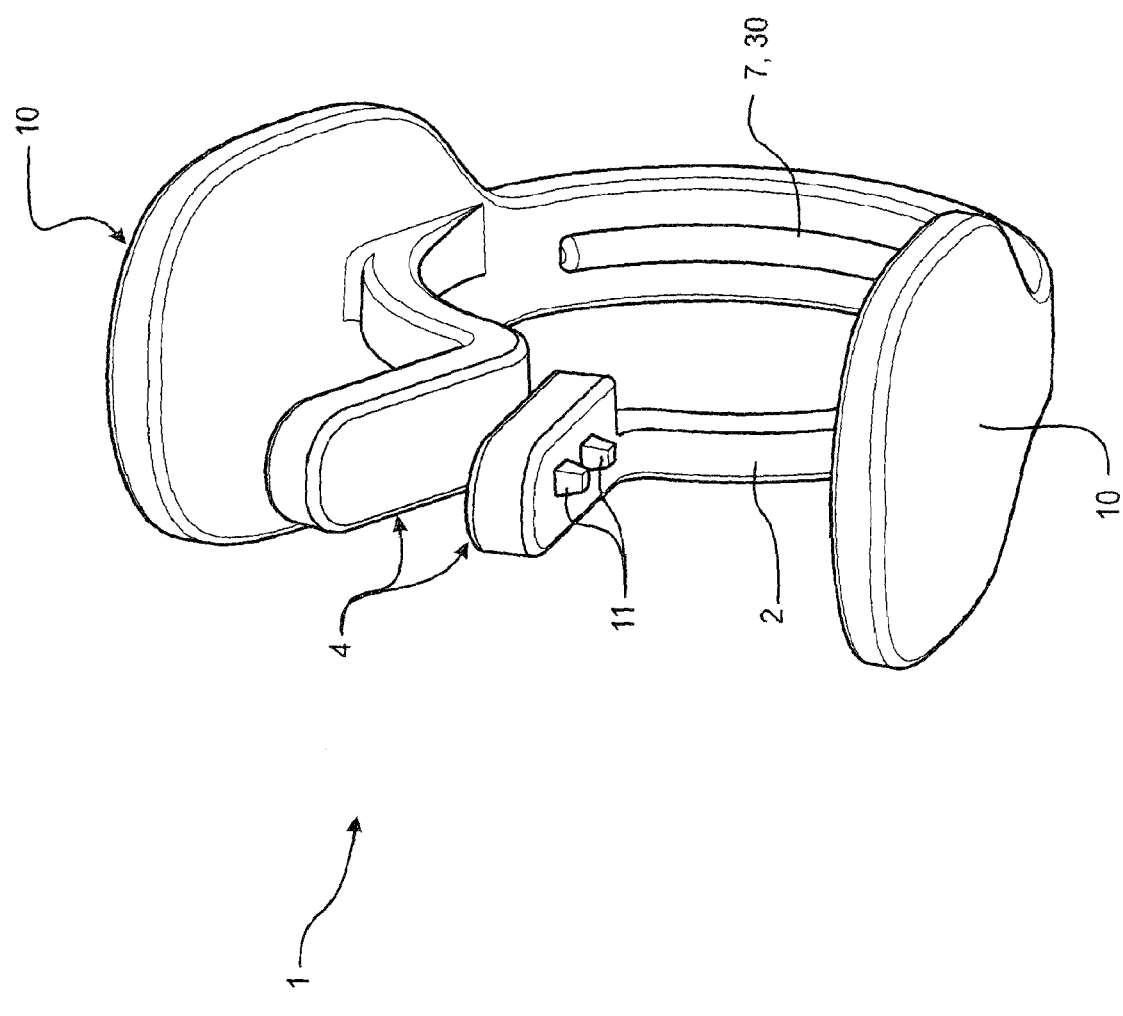
FIG. 10 is a top perspective view of FIG. 8, showing annular rib and teeth of the gripping jaws.

In a similar manner, FIGS. 8, 10 and 11 illustrate another component 1 embodiment, again where the jaws 4 are yet to be moved into their opposing relationship. FIG. 12 shows the opposing and inter-posed arrangement of the jaws 4 and grips of such a further embodiment.

The jaws 4 are openable and can receive and then close to grip an item enabling a more secure option for locating of the tube that is engaged by the component 1.

It will be appreciated this one or more feature, aspect or advantage of the invention provides for the re-positioning of the component 1 onto different items or objects, as and where a user desires most useful for comfort or other reasons.

Further, the component 1 allows the tube (and any attachments connected with the tube) to be re-positioned by moving of the tube when the component 1 is moved into the first body orientation that allows the component 1 to be moved along the tube (and about or from surface recess to recess or relief feature to feature) from a first set position to a second set position. When such a second set position is reached, the user re-orientates the component 1 such that the second body orientation is achieved to then prevent movement between the tube and component 1 (or at least to substantially resist movement between these). FIGS. 6A and 7A show the first orientation of a component relative to the recess or surface relief features or trough of a tube, while FIGS. 6B and 7B show component 1 when in a second orientation 6 relative to a tube's recesses or surface relief features or trough.

In one form, the portions of the body 2 engageable with the recesses 3 (or other surface relief features) are fixed or static portions of the body 2 (i.e. are not moveable). See for example the annular rib or lip portion 30 of FIGS. 8-13B, or portions 20, 22 of FIGS. 1-7B.

Various items or objects that the component 1 may be attached to (i.e. grip) includes one or more of the following: clothing, bedding, structures associated with personal clothing (e.g. personal lanyard, belt) or bedding (e.g. bed frame, mattress), structures associated with medical equipment or where a user is located (e.g. stands, bed side table), including incubators, and cots. It will be appreciated other items or objects can be used to attaching the component 1 to via the gripping jaws 4. Accordingly, when the component 1 is in the second orientation 6 and the jaws 4 are gripping of an item, the component 1 acts to locate the tube in a set position.

In other embodiments, a carer (e.g. mother, father or nurse) may hold a child or infant in a "kangaroo" style hold, and in such an instance the carer may attach the clip to their clothing such that tubing is supported without placing weight onto the patient interface and on to the child/infant.

As mentioned above, the body 2 can include a shoulder portion 10 (or finger tab portion) associated with each jaw of the pair of jaws 4. Such a shoulder portion 10 assists in providing a surface for actuation, by a user, of the jaws 4 to an open position 9. Such shoulder portion 10 can, for example, be an enlarged region of the body 2.

In use, shoulder portion 10 of the body 2 may be deflectable towards each other, such that, deflection moves the jaws 4 from a closed or substantially closed position 8 toward or to an open position 9. In return, release of the deflection provided by a user allows the hingedly biased jaws 4 to move back to a closed or substantially closed position 8. Advantageously, the shoulder portion 10 can be sized for relative ease of actuation by the fingers of a user, i.e. being finger tabs.

In respect of the jaws 4 of the component 1, one or each jaw can include a grip or grips for gripping (e.g. frictionally) of an item or object. In one form, the grips are one or a series of ridges, projections or teeth 11. Such jaw grips are preferably interlocking or inter-lockable (or interposing) with one or more corresponding grips of an opposing or other jaw.

In another embodiment, one of more of the grips can be shaped so as to expose one (or a series) of acute angled portions that face inwardly toward the body. Such acutely shaped portions may assist in helping to grip or grab the textile of a cloth (e.g. clothing or bedding sheets). This may for example be facilitated by the acute angled portions penetrating or semi-penetrating the weave of the cloth or fabric to which the grips are attached or becoming embedded into.

In yet a further embodiment, although it should be recognised such a feature may be provided in combination with the acutely shaped portions discussed above, one of more of the grips may be shaped so as to expose one (or a series of) obtusely angled portions facing outwardly away from the body. In such a configuration, advantageously the grips allow the ease of insertion of cloth or material into the mouth of the jaws, and therefore allowing the grips (when released from their open position) to engage with the cloth or material (or object). When provided in combination with the acutely shaped portions, sets of grips may be provided that allow the relative ease of insertion of material into the mouth of the jaws, yet the ability to easily remove the material from the grips is reduced by the improved gripping capability of the acutely shaped portions.

Such a component 1 may be formed of any suitable material allowing the above described features and deflection characteristics. It may be preferred that such a component 1 is however provided of a suitable, although not necessarily, medical grade material and, may for example, be of a suitable polymeric material.

In a further form, in the first orientation 5, the internal surface of the body 2 may comprise at least one first projection 20 engageable with a corresponding first recess of the tube or of a first respective tube, and at least one second projection 22 engageable with the same or another recess located near the first recess in which the at least one first projection 20 is engageable. And, in the second orientation 6, the internal surface of the body 2 may comprise at least one first 20 and at least one second projection(s) 22 that are engaged or engageable with a recess or recesses 3 (or other repeating surface relief features) of the tube, or respective tubes, such recesses separated from one another by a distance along the length of the or each respective tube.

When in the second orientation 6, this further form provides for the at least one first and at least one second projections 22 to act on the tube, or its recesses 3 or a part thereof (or surface relief features), to restrain (or resist) the component 1 from being moved between recesses 3 (or surface relief features) or along a length of the tube.

As illustrated by FIGS. 1-5, the component 1 comprises two first projections 20, and a single second projection 22. FIGS. 5-7B illustrate such a component 1 engageable with a tube and in the first and second orientation 6.

As shown by FIG. 6A in the first orientation 5, the two first projections 20 are engageable with a corresponding first recess of the tube, and the single second projection 22 is engageable with the same or another recess located near the first recess in which the at least one first projection 20 is engageable (i.e. in an orientation or position when the component 1 is able to be moved along the tube with relative ease).

As shown by FIGS. 6B and 7B in the second orientation 6, the two first projections 20 are engageable with a corresponding first recess of the tube, and the single second projection 30 is engageable with a recess of the tube separated from the first recesses 21 by a distance along the length of the tube (i.e. in an orientation or position when the component 1 is resistive to being moved along the tube).

In yet a further form, the component's body 2 can comprise of at least one lip for engaging with at least one recess of the tube, for example as illustrated by FIGS. 8-13B. In such a form, the lip can be one or a series of projections extending in a substantially annular from and about a surface of the body 2. Such a lip or lips are those portions of the body 2 that are engageable with the one or more external surface recesses 3 of the tube, as shown by FIGS. 11, 12. FIG. 13A illustrates such component when in a first orientation 5, where a second orientation 6 of such a component is similar to that as shown by FIG. 13B (but as shown in relation to a helically corrugated tube form). Similarly, the tube may be of axial corrugations (i.e. not helical), and the component 1 shown in FIG. 13A may be provided to operate in the manner (orientations) as shown by FIGS. 6A, 7A or when the tube has helical corrugations, as shown by FIGS. 7A, 7B.

As shown by FIGS. 15-20, the body 2 is engageable with one or more external surface recesses of respective one or more tubes (multiple tubes not shown, but body as shown is configured for receiving a pair of tubes). The body is configured, such that for each respective tube, at least one first projection 7, 20, 50 is engageable with a corresponding first recess of a respective tube. And, the body is also configured, such that for the same tube, at least one second projection 7, 22, 51 is engageable with the same first or another recess, of the same respective tube.

The component 1 shown by FIGS. 15-20, being of a multi-tube engaging body form, can be moved to be in the first orientation (e.g. the first orientation being as shown for example in relation to the single tube component embodiments of FIGS. 1-13B).

In such a first orientation, the internal surface of the body comprises, for each of the respective one or more tubes being engaged by the body, at least one first projection 7, 20, 50 engageable with a corresponding first recess of a respective tube, and at least one second projection 7, 22, 51 engageable with the same or another recess, of the same respective tube, located near the first recess in which the at least one first projection is engageable. Likewise, a further set of at least one first projections 7, 20, 60 and a further set of at least one second projection 7, 22, 61 is provided for engaging with a second tube. It will be understood that the body 2 may be adapted or shaped to receive and engage with one, two or more than two tubes.

In a second orientation, the internal surface of the body 2 comprises, for each of the respective one or more tubes that the body may be engageable with, at least one first 7, 20 projection(s) and at least one second projection(s) 7, 22 engaged with a recess or recesses of each respective tube, wherein the engaged recesses of each respective tube are separated from one another by a distance along the length of each of the respective tube(s). The first and second projections 50, 51 are used in relation to engaging of a first tube, while first and second further projections 60, 61 are used in relation to engaging of a second tube.

It will be appreciated the body 2 may be configured to engaged with additional tubes, such additional tubes would be engaged by further sets of first and second projections provided by an appropriately shaped body 2. For example, FIGS. 15-20 shows a component 1 having a body that is engageable with one or more external surface recesses (e.g. corrugations) of a pair of tubes (not shown). The body 2 of such an embodiment comprises at least one first projection 7, 20, 50 that is engageable with a corresponding first recess of a first respective tube, and at least one second projection 7, 22, 51 engageable with the same first or another recess, of the same first respective tube, and at least one further first projection 7, 20, 60 engageable with a corresponding first recess of a second respective tube, and at least one further second projection 7, 22, 61 engageable with the same first or another recess, of the same second respective tube.

FIG. 20 shows yet a further form of a component 1 configured for engaging with multiple tubes, in the embodiment shown, a pair of tubes. The body 2 is engageable with a pair of tubes via the portions or projections 7, the projections operating in the manner as described previously. A pair of opposing jaws 4 are provided that may be deflected into an open position by a user, with teeth 11 (not shown in FIG. 20) that can grip an item. In the embodiment shown, each one of the pair of tubes to be engaged are fitted into the distinct regions of the body 2. The body 2 comprises portions or projections 7 which engage with the external surface recesses of the tube. It will be appreciated such a component 1 may be shaped for engaging with only one, or two or more than two tubes. Such a component also comprises of a retainer 40, as will be described in more detail below.

In addition, it will be appreciated the various embodiments described above, and as illustrated, may include a retainer portion for retaining an accessory, for example an accessory that may be associated with the tube, such as an electrical cable or sensor cable (e.g. a temperature probe cable). The retainer portion may even be configured for receiving a lanyard such as those that may be looped about a user's neck for further supporting the weight held by the clip and grips when gripping an item. However, preferred forms for the retainer 40 include those where a cable may be friction fitted into the retainer portion or region. Such a retainer may be shaped to receive and hold cable in in-situ, such as a temperature probe cable that may be associated with a controller or control system for a heated or electrically powered medical breathing tube.

As shown in the embodiments of FIGS. 15-20, a retainer 40 is provided about an external surface of the body 2. Those embodiments illustrated by FIGS. 1-13B may also include a retainer, although are not specifically shown. It may also be appreciated that the retainer 40 portion may be provided about an internal surface of the body 2, appropriately positioned to be non-interfering with positioning or engaging of the tubes to which the body 2 is engageable.

The foregoing description of the invention includes preferred forms thereof. Modifications may be made thereto without departing from the scope of the invention.

The invention claimed is:

1. A locking tube clip for use with at least one tube, the locking tube clip comprising:
   a first region comprising an upper portion and a lower portion configured to circumscribe a portion of a first tube, wherein a first distance between the upper portion and the lower portion of the first region is configured for receipt of the first tube, an inner surface of the first region further comprising a first protrusion configured to engage with an undulating surface of the first tube;
   a second region comprising an upper portion and a lower portion configured to circumscribe a portion of a second tube, wherein a second distance between the upper portion and the lower portion of the second region is configured for receipt of the second tube, an inner surface of the second region further comprising a second protrusion configured to engage with an undulating surface of the second tube; and
   a gripping portion configured to attach the locking tube clip to an item, the item being different from the first tube or the second tube,
   wherein the first region and the second region of the locking tube clip are positioned in the same plane or in parallel planes, such that the first region and the second region of the locking tube clip are configured to position the first tube and the second tube substantially non-coaxial with one another and parallel to one another,
   wherein the gripping portion is moveable between an open position and a closed position.

2. The locking tube clip of claim 1, wherein the gripping portion comprises a pair of jaws, the pair of jaws deflectable between a closed position and an open position.

3. The locking tube clip of claim 1, wherein each of the inner surface of the first region and the inner surface of the second region comprises a substantially annular surface.

4. The locking tube clip of claim 1, wherein each of the inner surface of first region and the inner surface of the second region comprises a semi-annular surface.

5. The locking tube clip of claim 1, wherein the first distance between the upper portion and the lower portion of the first region defines a first opening, wherein the second distance between the upper portion and the lower portion of the second region defines a second opening, wherein the first opening and the second opening are diametrically opposed.

6. The locking tube clip of claim 1, further comprising a retainer for retaining an accessory.

7. The locking tube clip of claim 6, wherein the retainer is disposed on an external surface between the lower portion of the first region and the lower portion of the second region of the locking tube clip.

8. The locking tube clip of claim 6, wherein the retainer is disposed on an internal surface between the lower portion of the first region and the lower portion of the second region of the locking tube clip.

9. The locking tube clip of claim 1, wherein, in a first orientation, the first region and the second region are arranged in a first plane, such that the first region and the second region are substantially co-axial with the first tube and/or the second tube, wherein, in a second orientation, the first region and the second region are arranged in a second plane, different from the first plane, such that the first region and the second region are substantially non-co-axial with the first tube and/or the second tube.

10. The locking tube clip of claim 9, wherein the inner surface of the first region further comprises a third protrusion and the inner surface of the second region further comprises a fourth protrusion, wherein in the first orientation, the third protrusion is configured to engage the undulating surface of the first tube near the first protrusion, and the fourth protrusion is configured to engage the undulating surface of the second tube near the second protrusion.

11. The locking tube clip of claim 10, wherein in the second orientation, the first protrusion and the third protrusion are configured to engage the first tube at spaced apart locations along a length of the first tube, and wherein in the second orientation, the second protrusion and the fourth protrusion are configured to engage the second tube at spaced apart locations along a length of the second tube.

12. A locking tube clip for use with at least one tube, the locking tube clip comprising:
a first region comprising an upper portion and a lower portion configured to circumscribe a portion of a first tube, wherein a first distance between the upper portion and the lower portion of the first region is configured for receipt of the first tube, an inner surface of the first region further comprising a first protrusion configured to engage with an undulating surface of the first tube;
a second region comprising an upper portion and a lower portion configured to circumscribe a portion of a second tube, wherein a second distance between the upper portion and the lower portion of the second region is configured for receipt of the second tube, an inner surface of the second region further comprising a second protrusion configured to engage with an undulating surface of the second tube; and
a pair of jaws extending from the upper portion of the first region and the upper portion of the second region, the pair of jaws configured to attach the locking tube clip to an item, the item being different from the first tube or the second tube,
wherein the first region and the second region of the locking tube clip are positioned in the same plane or in parallel planes such that the first region and the second region of the locking tube clip are configured to position the first tube and the second tube substantially non-coaxial with one another and parallel to one another.

13. The locking tube clip of claim 12, wherein the pair of jaws comprises a series of ridges, projections, or teeth.

14. The locking tube clip of claim 12, wherein the pair of jaws are deflectable between a closed position and an open position.

15. The locking tube clip of claim 12, wherein each of the inner surface of first region and the inner surface of the second region comprises a semi-annular surface.

16. The locking tube clip of claim 12, wherein each of the inner surface of the first region and the inner surface of the second region comprises a substantially annular surface.

17. The locking tube clip of claim 12, wherein the first distance between the upper portion and the lower portion of the first region define a first opening, wherein the second distance between the upper portion and the lower portion of the second region define a second opening, wherein the first opening and the second opening are diametrically opposed.

18. The locking tube clip of claim 12, wherein, in a first orientation, the first region and the second region are arranged in a plane, such that the first region and the second region are substantially co-axial with the first tube and/or the second tube, wherein, in a second orientation, the first region and the second region are arranged in a second plane, such that the first region and the second region are substantially non-co-axial with the first tube and/or the second tube.

\* \* \* \* \*